United States Patent [19]

Tuba et al.

[11] 4,177,190
[45] Dec. 4, 1979

[54] DIAMINO-ANDROSTANES AND A PROCESS FOR THE PREPARATION OF THE SAID COMPOUNDS

[75] Inventors: Zoltán Tuba; Maria Marsai; Katalin Biro; Lászlo Szporny; Egon Karpati; Szabolcs Szeberényi, all of Budapest, Hungary

[73] Assignee: Richter Gedeon Vegyeszeti Gyar Rt., Budapest, Hungary

[21] Appl. No.: 886,450

[22] Filed: Mar. 14, 1978

Related U.S. Application Data

[63] Continuation of Ser. No. 709,325, Jul. 28, 1976, Pat. No. 4,101,545

[30] Foreign Application Priority Data

Aug. 1, 1975 [HU] Hungary ................. RI 575

[51] Int. Cl.$^2$ ................................ C07J 43/00
[52] U.S. Cl. .................. 260/239.5; 260/239.55 R; 424/241
[58] Field of Search ...................... 260/239.5

[56] References Cited
FOREIGN PATENT DOCUMENTS 1398050 6/1975 United Kingdom ................. 260/239.5

Primary Examiner—Elbert L. Roberts
Attorney, Agent, or Firm—Karl F. Ross

[57] ABSTRACT

Curare-type salts of the formula

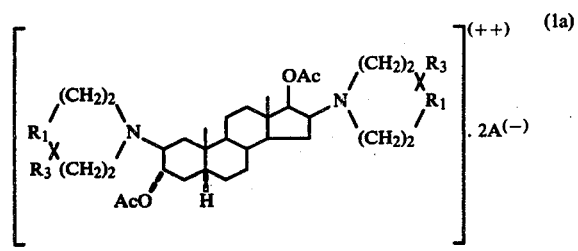

or

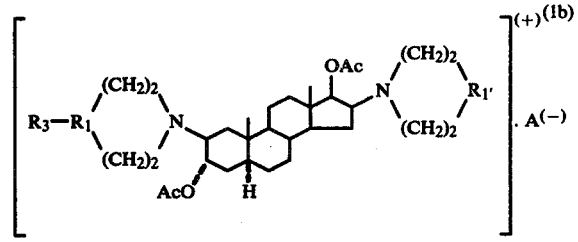

wherein
Ac is an alkyl carbonyl group containing 1 to 4 carbon atoms in the alkyl moiety and one of
$R_1$ and $R_2$, is a methylene group and the other is a group of the formula $>N-R_2$ wherein $R_2$ is an alkyl group containing 1 to 3 carbon atoms,
A is halogen and
$R_3$ is an alkyl group containing 1 to 4 carbon atoms, or an alkyl group; and
a process for the preparation thereof are disclosed.

10 Claims, No Drawings

DIAMINO-ANDROSTANES AND A PROCESS FOR THE PREPARATION OF THE SAID COMPOUNDS

This is a continuation of application Ser. No. 709,325, filed 28 July 1976 now U.S. Pat. No. 4,101,545.

The invention relates to new diamino-androstane derivatives, the acid addition salts and quaternary salts thereof and to a process for the preparation of the compounds.

The new diamino-androstane derivatives have the formula

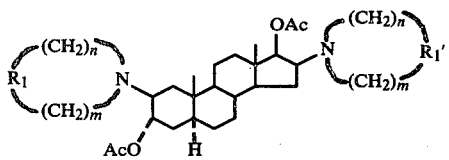

wherein

Ac is an alkylcarbonyl group containing 1 to 4 carbon atoms in the alkyl moiety, and one of $R_1$ and $R_1'$ is a methylene group and the other is a $>N-R_2$ group, wherein $R_2$ is a $C_{1-3}$ alkyl group n is 1 or 2 and m is 1, 2, 3 or 4.

The di-quaternary salts of the said diamino-androstanes have the formula

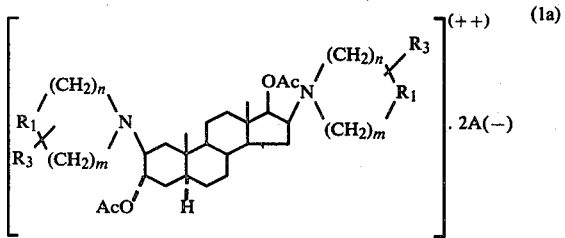

wherein

Ac, $R_1$, $E_1'$, n and m have the same meanings as defined above.

A is halogen and $R_3$ is alkyl having 1 to 3 carbon atoms or an allyl group.

The mono-quaternary salts of the compounds of the formula I have the formula

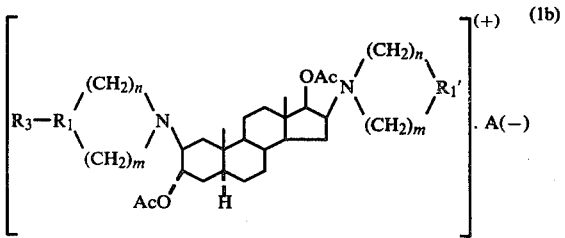

wherein

Ac, n, m, A and $R_3$ have the same meanings, as defined above.

$R_1'$ is methylene and $R_1$ is a $>N-R_2$ group, wherein $P_2$ has the same meaning as defined above.

The compounds of the formula I of the present invention are asymmetrical diamines, due to the different meanings of $R_1$ and $R_1'$, i.e. the two amines attached to the sterane nucleus at the 2β and 16β positions are different, one is a heterocyclic amine compound containing one nitrogen atom and the other amine contains two nitrogen atoms.

In the case of the new di-quaternary salts of the formula Ia regarding the position of $R_3$ the two groups deriving from the quaternizing agent are different. One of the $R_3$ groups is on the heterocyclic amino group containing one nitrogen atom ($R_1$ or $R_1'$ is methylene) and is attached to this single nitrogen and the other $R_3$ is on the heterocyclic amino group containing two nitrogen atoms ($R_1$ or $R_1'$ is a $=N-R_2$ group) and is attached to that nitrogen atom which bears the substituent $R_2$.

In case of the new mono-quaternary salts of the general formula Ib, $R_3$ is always attached to the heterocyclo containing two nitrogen atoms ($R_1$ or $R_1'$ is $=N-R_2$), at the nitrogen atom, which bears the substituent $R_2$.

All the compounds of the formulae I, Ia and Ib are new, and the intermediate products of the synthesis of the formulae II, III and IV are also new. The method for the preparation of the compounds of the formula V used as starting materials is described in Example 1.

The compounds of the formula I are biological active, and the quaternary salts of the formulae Ia and Ib an outstanding curare type compounds. The intensity of their activity surpasses the activity of the known compounds of similar effect.

The compounds of the formulae Ia and Ib show curare type, non-depolarizing neuro-muscular blocking effect, i.e. they inhibit the inplant of the nervous impulse on the striated muscle, do not cause hystamine release, do not decrease blood pressure and their effect can be stopped by neostigmine. The compounds do not show any hormonal effect.

To determine the intensity and the duration of the activity, cats subjected to anaesthesia and artificial respiration were tested.

The peroneus nerve was irritated electrically and the contraction of the tibialis muscle was registered, by intravenous administration of different doses of the blocking substances the dose inhibiting completely the muscle contraction ($ED_{100}$) was determined. The time between the starging effect and the restoration of the normal muscle reaction was measured. The data of the following table are related to the dose causing complete inhibition. As a referential substance pancuronium bromide (Negwer (1971) 4821) was used. (Advances in Steroid Biochemistry and Pharmacology (Briggs), W. R. Buckett: Aspects of the Pharmacology of Aminosteroids. 56–59, Br. J. Pharmac. Chemother 32. 671–682 (1968). Arzneimittel-Forsch. 19, 1723–1726 (1969).

| Compound | $ED_{100}$/mcg/kg | Duration of effect/minutes |
|---|---|---|
| 2β-(4-Dimethyl-piperazino)-16β-N-methyl-piperidino-3α,17β-diacetoxy-5α-androstane-dibromide | 4.5 | 16 |
| 2β-N-Methyl-p-peridin-16β-(4-dimethyl-piperazino)-3α,17β-diacetoxy-5α-androstane-dibromide | 7.2 | 18 |
| Pancuronium bromide | 18.0 | 23 |

The table shows, that the effective doses of the new compounds are 2.5 to 4 times smaller than that of pancuronium bromide and the duration of the effect is about 30 to 40% shorter.

The new compounds of the invention can be used in the first place for facilitating the intubation, alleviating the muscle spasms in the shock therapy or for hypomyotomia in any spasmodic diseases of the striated muscles.

The present invention is further directed to a process for the preparation of the compounds of the formula I—wherein Ac, $R_1$ and $R_1'$, n and m are as defined above, and of the diquaternary salts thereof of the formula Ia—wherein Ac, $R_1$, $R_1'$, n and m, A and $R_3$ are as defined above or of the mono-quaternary salts thereof of the formula Ib, wherein the substituents are as defined above, which comprises reacting a compound of the formula

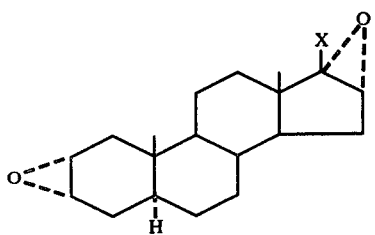

wherein X is halogen, with a compound of the formula

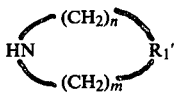

wherein n and m are as defined above and $R_1'$ is methylene or $>$N-$R_2$—
wherein $R_2$ is given above and adding, if desired a hydrogen halogenide to the reaction mixture and reducing the obtained compound of the formula

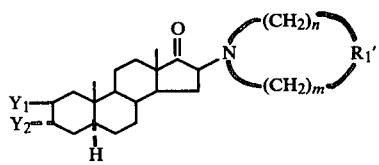

wherein n and m are as defined above, $R_1'$ in methylene or $>$N-$R_2$—
wherein $R_2$ is a $C_{1-3}$ alkyl, $Y_1$ is halogen, $Y_2$ is hydroxyl or $Y_1$ and $Y_2$ form together epoxy, and reacting the compound of the formula

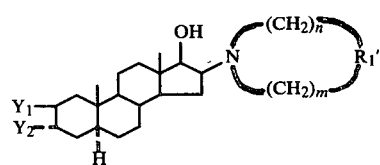

thus formed—wherein $R_1'$, n, m, $Y_1$ and $Y_2$ are given above with a compound of the formula

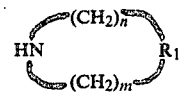

wherein $R_1$, n and m have the same meanings as given above and acylating the obtained compound of the general formula

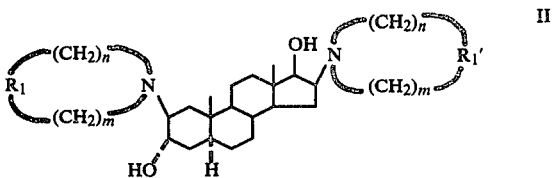

wherein $R_1$, $R_1'$, n and m have the same meanings as given above—with an aliphatic acarboxylic acid containing 1 to 5 carbon atoms or a reactive derivative thereof, and converting, if desired, the compound of the formula I thus obtained into an acid addition salt or into a quaternary salt thereof of the formula Ia or Ib.

The new compounds of the invention are prepared from 17-halo-androsta-2,16-diene of the formula V, preferably from the 17-iodo or 17-bromo derivative and from a heterocyclic amine of the formula VI.

The compounds of the formula VI are five to eight membered heterocyclic amines containing 2 nitrogens and the most advantageous representatives thereof are for example N-alkyl-piperazine, N-alkyl-pyrimidine, N,alkyl-imidazolidine, piperidine, pyrrolidine, heptamethylene imine etc. The alkyl chain of the N-alkyl derivatives contain 1 to 3 carbon atoms.

The compound of the formula V or VI is reacted alone or in the presence of an organic solvent, preferably acetonitrile or benzene, at a temperature in the range of from 10° C. to the boiling point of the reaction mixture. The reaction is accomplished within 20 to 70 hours at room temperature and within 10 to 120 minutes at the boiling point of the reaction mixture.

The compound of the formula IV obtained after the reaction is complete—wherein $Y_1$ and $Y_2$ stand together for epoxy—is isolated by evaporation or by extraction and is purified, if desired, by crystallization.

According to another preferable embodiment of the process of the invention the reaction mixture obtained after the reaction of the compounds of the formulae V and VI, is evaporated and the residue is dissolved in an inert organic solvent, preferably in an ether or chlorinated hydrocarbon and a hydrogen halogenide is added to the obtained solution. The hydrogen halogenide salt of the compound of the formula IV containing halogen as $Y_1$ and hydroxyl as $Y_2$ is separated from the reaction mixture. This method is mainly applied when the compounds of the formula IV can not be isolated in the form of a base by a simple method. The compound of the formula IV obtained by any of the previous methods, is reduced. As a reducing agent alkali metal borohydrides or alkoxy metal hydrides e.g. sodium borohydride, sodium-bis-(2-methoxy-ethoxy)-lithium-aluminiumhydride or -borohydride or -trimethoxyborohydride may be used. The reduction is conducted in an organic solvent, preferably in a lower aliphatic alcohol or chlorinated hydrocarbon or preferably in a mixture of both. The reduction is carried out at a temperature of below 30° C. When using the starting material of the formula IV in the form of a halogen acid-addition salt, an acid binding agent e.g. an alkali metal hydroxide or an alkali metal carbonate is also added.

As a reaction product a compound of the formula III is formed, which is isolated for example by evaporation or filtration, and is purified, if desired, by crystallization or by stirring and/or heating the mixture with a solvent dissolves the impurities but not the product.

The formed compound of the formula III is repeatedly reacted with an amine of the formula VI. The amine of the formula VI used for the second time contains a different substituent $R_1$. The amine of the formula VI is used in a large excess related to the compound of the formula III i.e. in a molar ratio of 1:40 to 1:50. The reaction is conducted in a bomb tube, preferably in the presence of water at an environmental temperature of 70° to 160°C., 130–150° C. at a pressure of a few atmospheres, preferably at the tension of the mixture itself corresponding to the temperature. The compound of the formula II thus obtained is isolated from the reaction mixture by evaporation or by pouring the compound of the formula II, preferably into water when using a starting material of the formula VI of higher boiling point, and by salting it out.

The compound of the formula II prepared according to the method described above is converted to the compound of the formula I by acylation.

The acylation may be conducted in an inert organic solvent, preferably in the presence of a tertiary amine, for example in pyridine. As acylating agents aliphatic carboxylic acids having 1 to 5 carbon atoms or preferably reactive derivatives of aliphatic carboxylic acids of 1 to 5 carbon atoms e.g. the corresponding acid halogenides or acids anhydrides and be used.

According to a preferable embodiment of the process the acylating agent is used as a solvent, preferably an aliphatic carboxylic acid of 1 to 5 carbon atoms and/or the corresponding acid anhydride, preferably acetic acid anhydride or propionic acid anhydride or a Lewis acid in a catalytical amount such as iron(III)chloride, antimony chloride, tin chloride or, preferably zinc chloride is added to the solution. The formed compound of the formula I may be isolated from the reaction mixture by alkalizing the mixture to pH=10 followed by purification. Pharmaceutically acceptable, non-toxic organic or inorganic acid addition salts can be formed, if desired, from the compounds of the formula I. Among the inorganic acid-addition salts, preferably halogen acid-addition salts, and among the organic acid addition salts acetates and gluconates are preferred.

Di-quaternary and mono-quaternary salts of the formulae Ia and Ib may be formed if desired, from the compound of the formula I. In order to obtain the quaternary salts the compounds of the formula I may be reacted with alkyl halides of 1 to 5 carbon atoms e.g. methyl, ethyl, propyl, i-butyl halides, preferably with the corresponding bromo-compound or allyl halides, preferably allyl bromide.

The quaternary salts are formed in an inert organic solvent e.g. in chlorinated hydrocarbons, preferably methylene chloride, in acetone, nitromethane, acetonitrile, etc.

The reaction is conducted at atmospheric pressure at a temperature in the range of from room temperature to the boiling point of the mixture or in a bomb tube under pressure, preferably at the tension of the mixture itself corresponding to the temperature.

The obtained product is isolated by filtration or by evaporation of the mixture or by adding acetone or diethylether to the reaction mixture and isolating the precipitated salt.

When preparing mono-quaternary salts of the formula Ib the quaternizing agent is used in a small excess and the starting material is dissolved in a small amount of solvent and thus the formed mono-quaternary salt is precipitated from the reaction mixture in the instant of its formulation.

When preparing diquaternary salts of the formula Ia in the quaternizing agent is used in a 10 to 20-fold molar access.

The details of this invention are illustrated by the following Examples:

EXAMPLE 1

2α,3α-epoxy-17-oxo-16β-N-methyl-piperazino-5α-androstane.

25 g. (0.068 mole) of 2α,3α,16α,17α-diepoxy-17β-bromo-5α-androstane are dissolved in 170 ml. of acetonitrile, whereafter 20.5 ml. (0.190 mole) of N-methyl-piperazine are added. The reaction mixture is allowed to stand for 24 hours and heated under reflux for 15 minutes. The reaction mixture is evaporated to dryness at reduced pressure and the residue is dissolved in methylene chloride. The methylene chloride solution is washed with water until the pH achieves the value of 7, followed by the separation of the 2 layers. The organic layer is dried over sodium sulfate, filtered and the filtrate is evaporated at reduced pressue. The residue is purified by stirring with ether, the crystallized product is filtered and dried.

Yield: 20.1 g. (76.5%) of 2α,3α-epoxy-17-oxo-16β-N-methyl-piperazino-5α-androstane. M.p.: 132–134° C.
$[\alpha]_D^{25} = +121.2°$ (c=1, in chloroform).

Analysis for the formula $C_{24}H_{38}N_2O_2$: Calculated: C, 74.60%; H, 9.85%; N, 7.24%. Found: C, 74.39%; H, 9.97%; N, 7.12%.

2α,3α,16α,17α-epoxy-17β-bromo-5α-androstane used as the starting material is prepared as follows:

200 g. (0.735 mole) of 17-oxo-5α-androst-2-ene are dissolved in 2000 ml. of ethanol, whereafter 360 ml. of triethylamine and 880 ml. of 98% hydrazine hydrate (14.7 mole) are added. The reaction mixture is heated under reflux for 2 hours and cooled to room temperature. The reaction mixture is then added under vigorous stirring to 20 l. of icy water. The precipitated product is filtered, washed with water to remove triethylamine and dried over phosphorus pentoxide in vacuo at room temperature. The crude product is recrystallized from n-hexane.

Yield: 185 g. (91%) of 17-hydrazone-5α-androst-2-one.

M.p.: 124° to 132° C.
$[\alpha]_D^{25} = +98°$ (c=1, in chloroform).

Analysis for the formula $O_{19}H_{30}N_2$: Calculated: C, 79.60%; H, 10.50%; N, 9.70%. Found: C, 79.42%; H, 10.60%; N, 9.61%.

30 g. (0.100 mole) of 17-hydrazone-5α-androst-2-ene are dissolved in 200 ml. of anhydrous pyridine and the solution is cooled to −10° C. A solution of 30 g. (0.168 mole) of N-bromo-succinic imide in 330 ml. of pyridine are added at 0-(−10) ° C. The reaction mixture is stirred until nitrogen evolution ceases and added to 3 l. of 5% icy hydrochloric acid solution. The precipitated substance is extracted with 300 to 400 ml. of carbon tetrachloride and the carbon tetrachloride layers are obtained. The combined tetrachloride solution is washed with 5% aqueous hydrochloride acid solution and with water until pH=7. The neutral carbon tetrachloride solution is dried over sodium sulfate, filtered, and the filtrate is evaporated to dryness. The oily residue is trituated with 100 ml. of n-hexane and the precipitated by-product is filtered. The filtrate is evaporated and the residue is triturated with 50 ml. of a 9:1 mixture of ethanol and acetone. The precipitated product is filtered and dried.

Yield: 23.4 g. (66%) of 17-bromo-5α-androsta-2,16-diene.

M.p.: 76–77° C.

$[\alpha]_D^{25} = 71.2°$ (c=1, in chloroform).

Analysis for the formula $C_{19}H_{27}Br$: Calculated: C, 71.35%; H, 8.07%; Br, 23.80%. Found: C, 71.21%; H, 8.15%; Br, 23.57%.

17-hydrazone-5α-androst-2-ene and N-iodo-succinic imide are reacted as described above to give the corresponding iodo compound.

Yield: 66% of 17-iodo-5α-androsta-2,16-diene.

M.p.: 71–72° C.

$[\alpha]_D^{25} = 56.1°$ (c=1. in chloroform).

Analysis for the formula $C_{19}H_{27}J$:

Calculated: C, 59.70%; H, 7.07%; J, 33.13%.

Found: C, 59.52%; H, 6.90%; J, 32.9%.

90g. (0.27 mole) of 17-bromo-5α-androsta-2,16-diene are dissolved in 1100 ml. of chloroform and a 7.2% solution (0.81 mole) of m-chloro-perbenzoic acid in 1600 ml. of chloroform are added to room temperature. The reaction mixture is allowed to stand at room temperature for 24 hours whereafter the mixture is cooled to 0° C. and under cooling with ice a 10% aqueous sodium hydroxide solution and water are added to remove the acid and to achieve a pH=7. After separation the chloroform layer is dried over sodium sulfate, filtered and the filtrate is evaporated to dryness. The oily residue is triturated with 100 ml. of ether, filtered and the crude product on the filter is recrystallized from acetonitrile.

Yield: 85.7 g. (87%) of 2α,3α,16α,17α-diepoxy-17β-bromo-5α-androstane.

M.p.: 160–162° C.

$[\alpha]_D^{25} = +73.5°$ (c=1, in chloroform).

Analysis for the formula $C_{19}H_{27}BrO_2$ Calculated: C, 62.00%; H, 7.35%; Br, 21.80%.

Found: C, 61.79%; H, 7.20%; Br, 21.7%.

2α,3α,16α,17α-diepoxy-17β-iodo-5α-androstane can be prepared by the method described above with a yield of 81% from 17iodo-5α-androsta-2,16-diene.

EXAMPLE 2

2β-chloro-3α(-hydroxy-17-oxo-16β-piperidino-5α-androstane-hydrochloride 12.5 g. (0.034 mole) of 2α,3α,16α,17α-diepoxy-17-bromo-5α-androstane are dissolved in 85 ml. of acetonitrile, whereafter 10 ml. (0.1 mole) of piperidine are added. The reaction mixture is heated under reflux for 1 hour, and the reaction mixture is evaporated at reduced pressure. The residue is dissolved in diethylether and the ether solution is washed with water until pH=7. The two layers are separated. The product is precipitated from the organic layer with 6% ethereal hydrochloric acid solution in the form of a chlorohydrate salt. The precipitated acid addition salt is filtered, washed with ether and dried in vacuo at 60°.

Yield 10.3 g. (70%) of 2β-chloro-3α-hydroxy-17-oxo-16β-piperidino-5α-androstane-hydrochloride.

M.p.: 237–239° C. (decomposition).

Analysis for the formula $C_{24}H_{39}O_2NCl_2$:

Calculated: C, 64.8% ; H, 8.7 %; Cl, 16.0 %.

Found: C, 64.6 %; H, 9.0 %; Cl, 15.7 %.

EXAMPLE 3

2α,3α-epoxy-17β-hydroxy-16β-N-methyl-piperazino-5α-androstane 15 g. (0.038 mole) of 2α,3α-epoxy-17-oxo-16β-N-Methyl-piperazino-5α-androstane are dissolved in the mixture of 45 ml. of methylene chloride and 120 ml. of methanol, whereafter 12 g. (0.31 mole) of sodium borohydride are added at a temperature of below 30° C. When the addition is complete, the product of the reduction is crystallized. The crystalline solution is stirred vigorously for 12 hours, whereafter the solvent is distilled at reduced pressure at a temperature of below 40° C. The residue is triturated with water, the crystallized product is filtered, dissolved in chloroform and washed with 5% aqueous sodium hydroxide solution and with water until pH=7. The layers are separated. The chloroform layer is dried on sodium sulfate, filtered and the filtrate is evaporated to dryness. The residue is recrystallized from acetonitrile.

Yield: 11.7 g. (77.2%) of 2α,3α-epoxy-17β-hydroxy-16β-N-methyl-piperazino-5α-androstane.

M.p.: 149–153° C.

$[\alpha]_D^{25} = +27.1°$ (c = 1. in chloroform).

Analysis for the formula $C_{24}H_{40}N_2O_2$;

Calculated: C, 74.20 %; H, 10.30 %; N, 7.22 %.

Found: C, 74.01 %; H10.41 %; N, 7.07 %.

EXAMPLE 4

2β-chloro-3α, 17β-dihydroxy-16β-piperidino-5α-androstane 25 g. (0.056 mole) of 2β-chloro-3α-hydroxy-17-oxo-16β-piperidino-5α-androstane-hydrochloride are dissolved in the mixture of 52 ml. of methylene chloride and 125 ml. of methanol. Under vigorous stirring 2.75 g. (0.069 mole) of pulverized audium hydroxide and at a temperature of 15–20° C. 12.5 g. (0.33 mole) of sodium borohydride are added to the solution. The product precipitated immediately. The crystalline solution is stirred for 5 hours, whereafter the product is filtered and washed with water. The mother liquor is evaporated at reduced pressure at a temperature of below 30° C., the residue is triturated with water, the mixture is filtered and the second crop above the filter is washed with water. The 2 fractions are combined. dried in vacuo at 50° C., followed by recrystallization from acetone.

Yield: 20.2 g. (88%) of 2β-chloro-3α-17β-dihydroxy-16β-piperidino-5α-androstane.

M.p.: 232–234° C.

Analysis: for the formula $C_{24}H_{40}ClO_2N$:

Calculated: C, 70.3%; H, 9.7 %; Cl, 8.6 %.

Found: C, 70.0 %; H, 9.9 %; Cl, 8.8 %.

EXAMPLE 5

2β-piperidino-16β-N-methyl-piperazino-3α,17β-dihydroxy-5α-androstane 14.8 g. (0.03 mole) of 2α,3α-epoxy-17β-hydroxy-16β-N-methyl-piperazine-5α-androstane are dissolved in 168 ml. (1.65 mole) of piperidine and 24 ml. of water, whereafter the reaction mixture is heated in a bomb tube for 72 hours at an environmental temperature of 140° C. After the reaction is accomplished the reaction mixture is evaporated at reduced pressure. The residue is stirred in acetonitrile, filtered and the product above the filter is heated under reflux in acetonitrile. The crystallized product is filtered and dried.

Yield: 12.4 g. (69.0%) of 2β-piperidino-16β-N-methyl-piperazino-3α,17β-dihydroxy-5α-androstane.

M.p.: 154–156° C.

$[\alpha]_D^{25} = +84.5°$ (c = 1. in chloroform).

Analysis for the formula $C_{29}H_{51}N_3O_2 \cdot H_2O$: Calculated: C, 71.0%; H, 10.80%; N, 9.26%.

Found: C, 70.8%; H, 10.97%; N, 9.10%.

EXAMPLE 6

2β-N-methyl-piperazino-16β-piperidino-3α,17β-dihydroxy-5α-androstane

The compound was prepared according to Example 5 from 2β-chloro-3α-,17β-dihydroxy-16β-piperidino-5α-androstane and from N-methyl-piperazine.

Yield: 67.0% of 2β-N-methyl-piperazino-16β-piperidino-3α,17β-dihydroxy-5α-androstane.

M.p.: 230–234° C.

$[\alpha]_D^{25} = +81.7°$ (c = 1, in chloroform).

Analysis for the formula $C_{29}H_{51}N_3O_2 \cdot H_2O$:
Calculated: C, 71.0 %; H, 10.80 %; N, 9.26 %.
Found: C, 70.8 %; H, 10.70 %; N, 9.05 %.

EXAMPLE 7

2β-piperidino-16β-N-methyl-piperazino-3α,17β-diacetoxy-5α-androstane.

3g (0.0063 mole) of 2β-piperidino-16β-N-methyl-piperazino-3α,17β-dihydroxy-5α-androstane are dissolved in the mixture of 13 ml. of acetic acid andydride and 1 ml. of glacial acetic acid, whereafter 0.3 g. of zinc chloride is given to the solution. The reaction mixture is stirred for 12 hours, whereafter the excess acetic acid andydride is decomposed by adding 40 ml. of water. The solution is cooled to 0° to 5° C. and 15 % aqueous sodium hydroxide solution is added at the same temperature until the pH reaches the value of 9–10. The precipitated fluffy substance is immediately extracted with ether. The ether extract is washed with an aqueous solution saturated with sodium chloride until neutral state. The layers are separated, the ether layer is dried over sodium sulfate and filtered. The filtrate is treated with 3 g. of decolourising silicagel, the mixture is filtered and evaporated to dryness. The product is crystallized from the residue by trituration with hexane, filtered and dried.

Yield: 2.6 g. (73.5%) of 2β-piperidino-16β-N-methyl-piperazino-3α,17β-diacetoxy-5α-androstane.

M.p.: 95–98° C.

$[\alpha]_D^{25} = +33.9°$ (c = 1, in chloroform).

Analysis for the formula $C_{33}H_{55}N_3O_4$:
Calculated: C, 71.20%; H, 3.00%; N, 7.54%.
Found: C, 71.01%; H, 8.87%; N, 7.36%.

EXAMPLE 8

2β-N-methyl-piperazino-16β-piperidino-3α-17β-diacetoxy-5α-androstane

The compound is prepared by acylation of 2β-N-methyl-piperazino-16β-piperidino-3α,17α-dihydroxy-5α-androstane according to the method described in Example 7.

Yield: 72.0%.

$[\alpha]_D^{25} = +29.4°$ (c = 1, in chloroform).

Analysis for the formula $C_{33}H_{55}N_3O_4$:
Calculated: C, 71.20%; H, 9.00%; N, 7.54%.
Found: C, 70.9%; H, 8.8%; N, 7.3%.

EXAMPLE 9

2β-N-methyl-piperidino-16β-(4-dimethyl-piperazino)-3β,17α-diacetoxy-5α-androstane-dibromide 1 g. (0.0018 mole) of 2β-piperidino-16β-N-methyl-piperazino-3α,17β-diacetoxy-5α-androstane is dissolved in 20 ml. of acetone whereafter 10 ml. of 5% solution of methyl bromide in acetone is added. The reaction mixture is allowed to stand for 48 hours at room temperature. The precipitated quaternary salt is filtered, triturated with acetone and ether and filtered. The filtered precipitation is heated under reflux in acetone, the crystalline solution is cooled to room temperature, filtered and dried.

Yield: 1.2 g. (87.2%) of 2β-N-methyl-piperidino-16β-(4-dimethyl-piperazino)-3α,17β-diacetoxy-5α-androstane-dibromide.

M.p.: 260–264° C. (decomposition).

Analysis for the formula: $C_{35}H_{61}N_3BrO_4 \cdot H_2O$:
Calculated: C, 55.00%; H, 8.24%; Br, 20.90%; N, 5.50%.
Found: C, 54.81%; H, 8.10%; Br, 20.51%; N, 5.40%.

EXAMPLE 10

2β-(4-dimethyl-piperazino)-16β-N-methyl-piperidino-3α,17β-diacetoxy-5α-androstane-dibromide 1.3 g. (2.34 mmole) of 2α-N-methyl-piperazino- 16β-piperidino-3α,17β-diacetoxy-5α-androstane are dissolved in the mixture of 10 ml. of acetone and 20 ml. of acetonitrile. 32 ml. of a solution of 8.4% methyl bromide (20 mmole) in acetone are added. The reaction mixture is allowed to stand for 98 hours at room temperature and the precipitated quaternary salt is isolated by the method described in Example 9.

Yield: 1.4 g. (78.5%) of 2β-(4-dimethyl-piperazino)-16β-N-methyl-piperidino-3α,17β-diacetoxy-5α-androstane-dibromide.

M.p.: 248–252° C. (decomposition).

$[\alpha]_D^{25} = +14.3°$ (c = 1, in chloroform).

Analysis for the formula $C_{35}H_{61}Br_2N_3O_4 \cdot H_2O$:
Calculated: C, 55.00%; H, 8.24%; N, 5.5%; Br, 20.9%.
Found: C, 54.75%; H, 7.96%; N, 5.42%; Br, 20.6%.

EXAMPLE 11

2β-(4-dimethyl-piperazino)-16β-piperidino-3α,17β-diacetoxy-5α-androstane-bromide 2 g. (3.6 mmole) of 2β-N-methyl-piperazino-16β-piperidino-3α,17β-diacetoxy-5α-androstane are dissolved in 20 ml. of acetone whereafter 12 ml. (10.6 mmole) of 8.4% methyl bromide in acetone are added. The reaction mixture is allowed to stand at room temperature, whereafter the precipitated quaternary salt is filtered, washed with acetone and ether and the precipitate is purified by mixing it with acetone, the mixture is filtered and dried.

Yield: 1.5 g. (62.5%) of 2β-(4-dimethyl-piperazino)-16β-piperidino-3α,17β-diacetoxy-5α-androstane-bromide.

M.p.: 234–237° C. (decomposition).

$[\alpha]_D^{25} = +12.8°$ (c = 1, in chloroform).

Analysis for the formula $C_{34}H_{58}BrN_3O_4 \cdot H_2O$:
Calculated: C, 61.4%; H, 8.7%; N, 6.1%; Br, 11.7%.
Found: C, 61.1%; H, 8.9%; N, 5.9%; Br, 11.3%.

What we claim is:

1. A process for the preparation of a di-quaternary salt of the formula

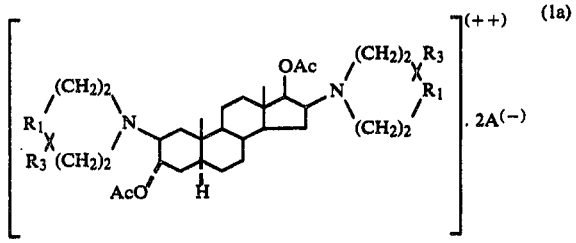

wherein
- Ac is an alkyl carbonyl group having 1 to 4 carbon atoms in the alkyl moiety, one of
- $R_1$ and $R_1'$ is a methylene group and the other is a group of the formula $>N-R_2$ wherein $R_2$ is a $C_{1-3}$ alkyl group,
- $R_3$ is an alkyl group containing 1 to 4 carbon atoms or an allyl group,
- A is halogen, or of a mono-quaternary salt of the formula

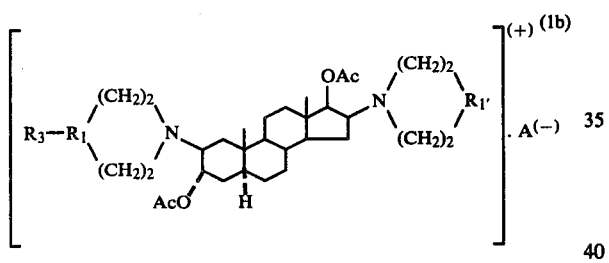

wherein
- Ac, A and $R_3$ have the same meaning as defined above,
- $R_1'$ is a methylene group and
- $R_1$ is a group of the formula $>R-R_2$ wherein $R_2$ is as defined above, which comprises selectively reacting the 16,17 epoxy group of a compound of the formula

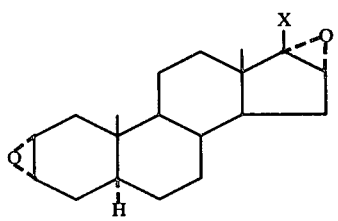

wherein X is halogen—with a compound of the formula

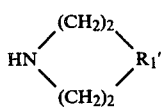

in the presence of a hydrogen halide wherein $R_1'$ is a methylene group or a $>N-R_2$ group to form a compound of the formula

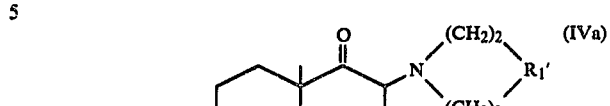
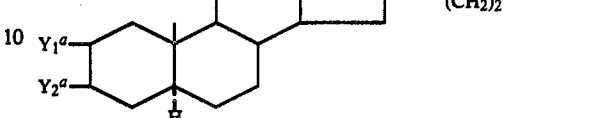

wherein $Y_1^a$ is halogen and $Y_2^a$ is hydroxy; or selectively reacting the 16,17-epoxy group of a compound of the formula

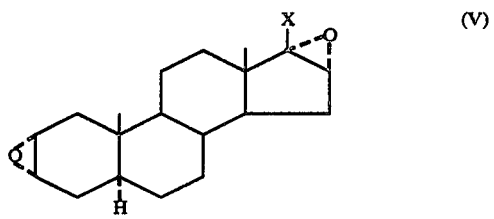

wherein X is halogen with a compound of the formula

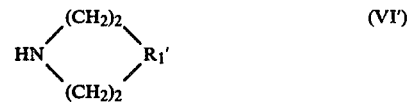

wherein $R_1'$ is a methylene group or a $N-R_2$ group, to form a compound of the formula

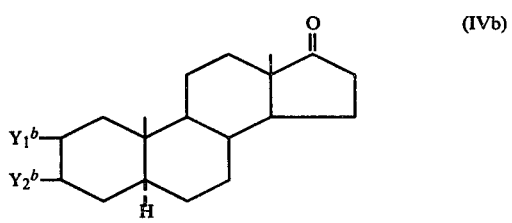

wherein $Y_1^b$ and $Y_2^b$ form together an epoxy group, and reducing the compound IVa or IVb to form a compound of the formula:

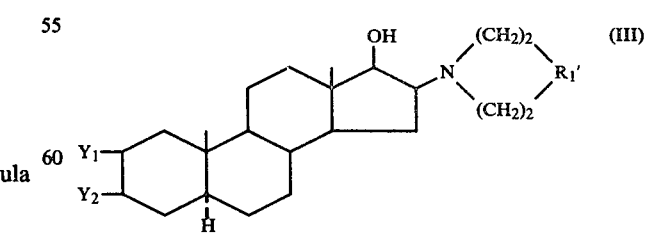

wherein $Y_1$ is halogen, $Y_2$ is hydroxyl or $Y_1$ and $Y_2$ form together an epoxy group;
reacting the compound formed above with a compound of the formula:

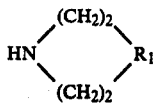

to yield a compound of the formula

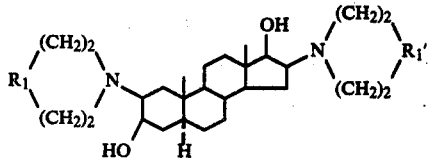

acylating the compound formed above with a $C_1$ to $C_5$ aliphatic carboxylic acid, $C_1$ to $C_5$ aliphatic carboxylic acid anhydride or $C_1$ to $C_5$ aliphatic carboxylic acid halogenide to yield a compound of the formula

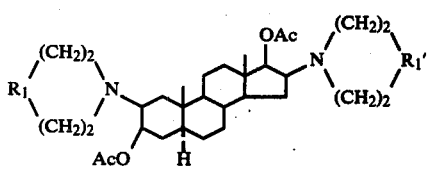

and converting the compound above into a quaternary salt thereof of the formula Ia or Ib.

2. A process as claimed in claim 1, which comprises reducing the compounds of the formulae IVa or IVb with a metal hydride.

3. A process as claimed in claim 1, which comprises conducting the reduction at a temperature of below 30° C.

4. A process as claimed in claim 1, which comprises reacting the compounds of the formulae III and IVa or IVb at a temperature of 70° to 160° C.

5. A process as claimed in claim 1, which comprises acylating the compound of the formula II with a $C_{1-5}$ acid anhydride.

6. A process as claimed in claim 1, which comprises acylating in the presence of a Lewis acid.

7. A process as claimed in claim 1, which comprises conducting the reactions in a solvent.

8. A process as claimed in claim 1, which comprises preparing 2β-N-methyl-piperidino-16β-(4-dimethyl-piperazine)-3α,17β-diacetoxy-5α-androstane-dibromide.

9. A process as claimed in claim 1, which comprises preparing 2β-(4-dimethyl-piperazino)-16β-N-methyl-piperidino-3α,17β-diacetoxy-5α-androstane-dibromide.

10. A process as claimed in claim 1, which comprises preparing 2β-(4-dimethyl-piperazino)-16β-piperidino-3α-17β-diacetoxy-5α-androstane-bromide.

* * * * *